(12) United States Patent
Lambl (10) Patent No.: US 6,955,908 B1
(45) Date of Patent: Oct. 18, 2005

(54) ORGANISM ASSOCIATED WITH NONGONOCOCCAL URETHRITIS

(76) Inventor: Barbara B. Lambl, 26 F Sea Breeze La., Nahant, MA (US) 01908

(*) Notice: Subject to any disclaimer, the term of this patent is extended or adjusted under 35 U.S.C. 154(b) by 21 days.

(21) Appl. No.: 09/598,604

(22) Filed: Jun. 21, 2000

(51) Int. Cl.$^7$ ............................ A61C 19/04; A61B 5/00
(52) U.S. Cl. ................... 435/243; 435/947; 435/7.36; 435/258.1; 436/516; 436/543; 436/165; 514/10; 514/12; 514/252; 604/11; 604/285; 128/758; 128/759
(58) Field of Search ................. 600/584, 572; 128/759, 758, 634; 606/46; 422/450; 514/10, 514/12, 252; 195/127; 73/343 R; 435/6, 435/947, 7.36, 258.1, 510, 243; 436/165, 436/516, 543; 433/72; 604/11, 285

(56) References Cited

U.S. PATENT DOCUMENTS

| | | | | |
|---|---|---|---|---|
| 2,664,879 A | * | 1/1954 | Hardy | |
| 3,822,593 A | * | 7/1974 | Oudewaal | 73/343 R |
| 3,875,015 A | * | 4/1975 | Wadley et al | 195/103.5 |
| 4,018,653 A | * | 4/1977 | Mennen | 195/127 |
| 4,105,500 A | * | 8/1978 | Libman et al. | 195/103.5 |
| 4,108,729 A | * | 8/1978 | Mennen | 195/127 |
| 4,951,684 A | * | 8/1990 | McMillian | 128/758 |
| 5,063,930 A | * | 11/1991 | Nucci | 600/366 |
| 5,300,491 A | * | 4/1994 | Andrews et al. | 514/10 |
| 5,425,377 A | * | 6/1995 | Caillouette | 128/759 |
| 5,474,997 A | * | 12/1995 | Gray et al. | 514/252 |
| 5,577,512 A | * | 11/1996 | Caillouette | 128/759 |
| 5,646,114 A | * | 7/1997 | Lambert, Jr. | 514/12 |
| 5,704,353 A | * | 1/1998 | Kalb et al. | 128/634 |
| 5,725,373 A | * | 3/1998 | Yeh | 433/72 |
| 5,738,654 A | * | 4/1998 | Tihon | 604/105 |
| 5,776,694 A | * | 7/1998 | Sheiness et al. | 435/6 |
| 5,827,200 A | * | 10/1998 | Caillouette | 600/584 |
| 5,928,165 A | * | 7/1999 | Caillouette | 600/572 |
| 5,965,453 A | * | 10/1999 | Skiffington et al. | 436/165 |
| 6,013,036 A | * | 1/2000 | Caillouette | 600/572 |
| 6,113,597 A | * | 9/2000 | Eggers et al. | 606/46 |
| 6,180,136 B1 | * | 1/2001 | Larson et al. | 424/450 |
| 6,214,548 B1 | * | 4/2001 | Relman et al. | 435/6 |
| 6,271,203 B1 | * | 8/2001 | Lambert, Jr. | 514/12 |
| 6,426,227 B1 | * | 7/2002 | Kritzman et al. | 436/43 |

OTHER PUBLICATIONS

Abou El Seoud, SF et al, Journal of the Egyptian Society of Parasitology, vol. 28(1), Apr. 1998, pp. 263-270.*

Birthistle, K et al, Genitourinary Medicine, vol. 72(6), p. 445.*

Suresh, K et al, Parasitology Res. vol. 79(6), pp. 456-460, 1993.*

Zumla, A et al, Parasitology, vol. 105, Suppl. pp. S93-S101, 1993.*

Lambl, BB et al, AIDS, Jun. 1996, vol. 10(7), pp. 739-744.*

Monteiro-Leal, LH et al, Cell Motility and the Cytoskeleton, vol. 34, pp. 206-214, 1996.*

Myjak, P et al, Wiadomosci parazytologiczne, 1997, vol. 43(2), pp. 163-170, (abstract only).*

(Continued)

Primary Examiner—Lynette R. F. Smith
Assistant Examiner—Ginny Allen Portner
(74) Attorney, Agent, or Firm—Clark & Elbing LLP; Paul T. Clark (57) ABSTRACT

The invention features a biologically pure culture of a newly identified single-celled organism Spiky Rotating Cells (SPR), methods to diagnose an SPR infection in a human patient, an instrument for collecting and detecting an SPR infection, and methods for treating an SPR infection.

16 Claims, 4 Drawing Sheets

OTHER PUBLICATIONS

Dunn, LA et al, International Journal of parasitology, vol. 19(1), pp. 43-56, Feb. 1989, (abstract only).*

Ruffer, U et al, Cell Motility and Cytoskeleton, vol. 37, pp. 111-119, 1997.*

Verges, J, Ann. Urol.. 1989, Voo. 23(4), pp. 343-344, (English abstract).*

Rappelli, R et al, The Lancet, vol. 352, p. 2023, Dec. 19-26, 1998.*

Cali, A et al, J. Euk. Microbiol. vol. 40(1), pp. 101-112, 1993.*

Soule, Jeremy B. et al, Arch. Pathol. Lab. Med. vol. 121 (8), Aug. 1997, pp. 880-887.*

Didier, ES et al, J. Euk Microbiol. vol. 43(1), Jan.-Feb., 1996, pp. 34-43.*

Mohammad, Al-Sanori Tarek, Mikrobiolohichnyi Zhurnal, vol. 58(2), pp. 64-69, 1996 (abstract only).*

Sobottka, I et al, Journal of Clinical Microbiology, vol. 33(11), pp. 2948-2952, Nov. 1995.*

Hartskeerl, RA et al, Parasitology, vol. 110, 1995, pp. 277-285.*

Ryu, JS et al, Korean Journal of parasitology, Dec. 1998, vol. 36(4), pp. 255-260, abstract only.*

Benchimol, M et al, European Journal of cell biology, vol. 80(9), pp. 593-607, Sep. 2001, abstract only.*

Abou El Seoud et al, Journal of Egyptian Society of Parasitology, vol. 28(1), Apr. 1998.*

Bush, William H. et al, American Journal of roentgenology, Apr. 1985, vol. 144(4), pp. 795-799.*

Monteiro-Leal, LH et al, Cell motility and the cytoskeleton, 1996, vol. 34(3), pp. 206-214.*

Birthistle, K etal, Genitourin Med., vol. 72, pp. 445-452.* van der Schee, Cindy et al, Journal of Clinical Microbiology, Dec. 1999, pp. 4127-4130, vol. 37(12).*

Volter, D. et al., Loop Suction Biopsy of the Urinary Bladder, Der Urologe Ausg. A (Germany) Sep. 1981. vol 20(s), p. 1278-281.*

Burstein et al., "Nongonococcal Urethritis—A New Paradigm," *Clin. Infect. Dis.* 28:S66-S73 (1999).

Dille et al., "Amplification of Chlamydia trachomatis DNA by Ligase Chain Reaction," *The Journal of Clinical Microbiology* 31:729-731 (1993).

Erbelding et al., "Urethritis Treatment," *Dermatologic Clinics* 16:735-738 (1998).

Hooton et al., "Prevalence of Mycoplasma Genitalium Determined by DNA Probe in Men with Urethritis," *The Lancet* 1:266-268 (1988).

Krieger, "Trichomoniasis in Men: Old Issues and New Data," *Sexually Transmitted Diseases* 22:83-95 (1995).

Martin et al., "A Controlled Trial of a Single Dose of Azithromycin for the Treatment of Chlamydial Urethritis and Cervicitis," *The New England Journal of Medicine* 327:921-925 (1992).

Martin et al., "Urethritis in Males," In: *Sexually Transmitted Diseases*, 3$^{rd}$ ed., (Holmes, Sparling Mardh, Lemon, Stamm, Piot, Wasserheit, eds), McGraw Hill, New York, p. 833-845 (1999).

Martinez-Garcia et al., "Protozoan Infections in the Male Genital Tract," *The Journal of Urology* 156:340-349 (1996).

Moritz et al., "Urethritis Associated with Disseminated Microsporidiosis: Clinical Response to Albendazole," *Clin. Infect. Dis.* 22:592-593 (1996).

Oriel, "Role of Genital Mycoplasmas in Nongonococcal Urethritis and Prostatitis," *Sexually Transmitted Diseases* 10s:263-270 (1983).

Schmid et al., "Evolving Strategies for Management of the Nongonococcal Urethritis Syndrome," *JAMA* 274:577-579 (1995).

Schwartz et al., "Etiology of Nongonococcal Nonchlamydial Urethritis," *Dermatologic Clinics* 16:727-733 (1998).

Stamm et al., "Azithromycin for Empirical Treatment of the Nongonococcal Urethritis Syndrome in Men: A Randomized Double-blind Study," *JAMA* 274:545-549 (1995).

Stary, "Urethritis—Diagnosis of Nongonococcal Urethritis," *Dermatologic Clinics* 16:723-726 (1998).

Swartz et al., "Diagnosis and Etiology of Nongonococcal Urethritis," *The Journal of Infectious Diseases* 138:445-454 (1978).

Taylor-Robinson, "The Role of Mycoplasmas in Non-Gonococcal Urethritis: A Review," *The Yale Journal of Biology and Medicine* 56:537-543 (1983).

Birthistle et al., "Microsporidia: A New Sexually Transmissable Cause of Urethritis," *Genitourinary Medicine* 72:445 (1996).

el Seoud et al., "Study of Trichomoniasis among Egyptian Male Patients," *Journal of Egyptian Society of Parasitology* 28:263-270 (1998).

Suresh, et al., "*In Vitro* Encystment and Experimental Infections of *Blastocystis hominis,*" *Parasitology Research* 79: 456-460 (1993).

* cited by examiner

ORGANISM ASSOCIATED WITH NONGONOCOCCAL URETHRITIS

BACKGROUND OF THE INVENTION

The most common sexually transmitted disease in men is nongonococcal urethritis (NGU). On average, 5 million new cases are reported annually in the United States alone. NGU is a syndromic diagnosis based on the finding of acute inflammation in the urethra. It has been linked to more than 10 different pathogenic species, including trichomonas, candida, herpes, and atypical bacteria. The most important pathogen, found in approximately half of cases, is *Chlamydia trachomatis*. In half of cases, however, no pathogen is identified.

Several lines of investigation have established *Chlamydia trachomatis* as the principal cause of NGU. *Chlamydia* has been isolated as the sole pathogen in 35–50% of cases. It is infrequently found in asymptomatic men. When present, it is usually associated with clear-cut pathology and inflammatory urethral smears. (However, it may also be harbored with minimal symptoms or signs in carriers.) Men with a history of disease have serologic evidence of specific immune response to the infection; and men with acute disease have increasing IgM serologic titers or seroconversion. Transmission of *Chlamydia* has been demonstrated in over 80% of female contacts of men with the infection, but only 11% of partners of negative men. Treatment with antichlamydial drugs eradicates the organism and cures the disease.

While the role of *Chlamydia* is well-established, the role of other pathogens is more controversial. The mycoplasmas have long been the subject of much investigation and debate. *Ureaplasma urealyticum* has been isolated in more than half of cases in some series (Tayler-Robinson, Hooton, Root, Munday, Stefanik). However, it is just as frequently found in completely asymptomatic men. And it is isolated more often in men who are sexually active than those who are not. There are three lines of evidence that have persuaded some, though by no means all, venerologists that *Ureaplasma* must be playing a role in at least some cases of NGU: 1) evidence from partial treatment trials in which disease recurs after therapy ceases (Shepard); 2) from differential treatment trials in which disease recurs after therapy ceases (Shepard); 3) from differential treatment trials where only one of two susceptible organisms is eradicated and disease persists (Prentice); and 4) from human inoculation and reinoculation trials (Tayler-Robinson). *Mycoplasma hominis*, although pathogenic in PID and cervicitis, has not been confirmed to cause urethritis. On the other hand, another *Mycoplasma* strain, *Mycoplasma genitalium*, has been associated with 15–40% of *Chlamydia*-negative NGU, and only 19% of controls.

Protozoal infection as a cause of NGU has been considered rare in the developed world. Infection rates are higher in the developing world, with series from Eastern Europe, Africa, Asia and South America reporting in the range of 10–15%. However, a more recent series from Seattle casts doubt on that presumption. Using rigorous methodology including selective cultures, Krieger was able to show *Trichomonas vaginalis* in 17% of men with NGU(Krieger). Other pathogens such as the anaerobic bacteria are associated with disease in women but not in men. Finally, the viruses, Herpes simplex, Human papillomavirus, and Adenovirus, have been associated, albeit rarely, with NGU. In sum, the known pathogens account for perhaps 40–75% of all cases of NGU.

No diagnosis is determined in 21–60% of cases of NGU (Janier, Jensen, Hooton, Root, Stefanik). While for many years *Chlamydia trachomatis* infection has been reported in the range of 35–50%, more recently Stamm, and others have pointed to a declining role for this pathogen (Stamm). In a large multicenter 1990 study, only 15% of cases were associated with *Chlamydia*, and fully 57% were unexplained (Stamm). Interestingly, while the prevalence of *Chlamydia* is declining, NGU is not. Therefore, the proportion of unexplained cases of NGU may actually be increasing (Zenilman, Schmid).

The reasons put forth for the culture-negative case fall into four broad categories: misdiagnosis, mechanical urethral processes, immunological processes, and unrecognized pathogens. The diagnosis of urethritis can be difficult to establish because of both underdiagnosis and overdiagnosis. The sensitivity of the urethral smear is variable. It may be affected by several factors including: the duration of symptoms, the adequacy of sampling, and the pathogen involved (Arya, Bowie, Landis, Shahmanesh, Swartz, Terry). Urethritis may be overdiagnosed in some men because of the persistence of symptoms after treatment or because of hypervigilance, even in the absence of inflammation (Martin). Some chronic cases of urethritis that are unresponsive to antibiotics may be associated with mechanical urethral problems, although this is rare(Krieger). The not infrequent observation that some men continue to have evidence of inflammation after successful treatment of urethritis has led some investigators to suggest that chronic urethritis, and particularly posttreatment urethritis, may be a consequence of local immunologic processes (Krieger, Martin & Bowie, Hooton, Taylor-Robinson). This is an area of ongoing investigation. Many of these same authorities allude to the possible existence of as yet unrecognized pathogens in NGU (Stamm, Schmid, Oriel, Taylor-Robinson).

In order to prove causality in NGU, Taylor-Robinson has set out several criteria that should be met. First the putative pathogen must be isolated more frequently or be found in greater numbers in men with NGU than in asymptomatic men. Second, when an appropriate antimicrobial agent is administered, and the infection is cleared, the symptoms of the disease must also resolve. Third, there must be objective evidence of an immune response to the offending pathogen. And lastly, the putative pathogen must be transmissible and cause comparable disease in the recipient. Of all the pathogens mentioned above, only *Chlamydia trachomatis, Mycoplasma genitalium*, and *Trichomonas vaginalis* fulfill all the criteria for pathogenicity in NGU. Neither a convincing antibody response nor overwhelming association with disease have been demonstrated in the case of *Ureaplasma urealyticum*. One other important caveat has been put forth by Taylor-Robinson, that a putative pathogen must be shown to be associated with disease in the absence of other pathogens. Numerous prior studies have been undermined by failure to control for other potential pathogens, in particular *Chlamydia*.

The treatment of NGU is made more difficult by the frequent absence of a definitive diagnosis. Many clinicians approach it as a syndrome and direct initial therapy at the most likely pathogens, *Chlamydia* and *Ureaplasma*. Studies have borne out the effectiveness of this approach in many cases. Doxycycline, long the treatment of choice, is effective against all strains of *Chlamydia* and most strains of *Ureaplasma*, although 10% of the latter are resistant. Martin demonstrated that a single dose of Azithromycin was comparable to Doxycycline in the treatment of uncomplicated chlamydial urethritis (Martin). More recently, Stamm and colleagues demonstrated that Azithromycin was overall as effective as Doxycyline, curing 78% of cases of NGU (Stamm). Of some concern, however, was their observation that only 47% of *Ureaplasma* cases responded to Azithromycin. Nevertheless, the convenience of unit dosing under direct supervision has made Azithromycin the preferred treatment in many STD clinics. Treatment failures have rarely been reported. In one series of treatment failures, Erythromycin cured 52% of men (Hooton). In a smaller series, Flagyl was used in refractory cases with good clinical efficacy (Toth).

SUMMARY OF THE INVENTION

In the course of caring for patients at the STD Clinic of the Boston Medical Center, I have observed an association between an unusual organism and NGU. Here I present my findings.

Men who presented to the STD clinic with urethral discomfort or discharge were screened for NGU. Twenty-five men with NGU were matched to 25 asymptomatic controls from the same clinic. (Asymptomatic men routinely present to the clinic for routine HIV testing or STD screening.) Cases and controls were sexually active men who were matched for age (+/−5 years) and sexual preference (heterosexual, homosexual, bisexual).

After informed consent was obtained, men were examined and urethral samples were obtained for microbiologic testing. Three urethral swabs were obtained, for Gram's stain, direct microscopy, culture for *Neisseria gonorrhea* on Thayer-Martin media in 5% $CO_2$ enriched atmosphere, and DNA amplification using the Ligase Chain Reaction methodology (LCX) for *Chlamydia trachomatis*. NGU was defined as laboratory evidence of urethral inflammation, evidenced by ≧4 PMNs/hpf on Gram's stain. Informed consent was obtained from all participants, and this study was conducted with the approval of the Institutional Review Board of the Boston Medical Center.

Of 28 men who presented to the clinic with urethral symptoms, 25 were found to have NGU. (Three men had gonorrhea and were excluded from the study.) All men had signs of inflammation on their urethral smear, with a mean polymorphonuclear cell (PMN) count of 15 (range 4–40).

Routine pathogens were identified in 10/25 men with NGU: 8 *Chlamydia*, 1 HSV, and 1 *Candida*. Fifteen men with NGU had no pathogen identified by standard laboratory methods.

Thirteen/fifteen men with no conventional pathogen were noted to have a distinctive single-celled organism in their urethral secretions. The organisms were round and motile. They were 7 $\mu$m–8 $\mu$m in size and had a highly refractile cell membrane, with characteristic spiky membrane projections. They moved in a peculiar rotatory fashion, translocating across the microscopic field. These organisms were present in large concentrations in urethral secretions, mean n=14/hpf (range 1–100). To my knowledge, these organisms have not previously been described, and for convenience, I have called them SPR, spiky rotating cells.

Nine of the men with known pathogens also had coinfection with this organism. Two men with NGU had no pathogens detected.

Among 25 asymptomatic controls, there were four genital infections diagnosed: two with *Candida balanitis*, one pediculosis pubis, and one secondary syphilis. None of the controls were found to have urethral inflammation. Two of the controls were found to have SPR in their urethral secretions. However, the organisms were rare in number, only 1–2 present on the entire slide.

In total, 22–25 men with NGU had SPR cells. Only 2 of 25 asymptomatic controls had SPR noted on examination. Men who were found to have SPR cells in urethral secretions were eighty-four times as likely to be diagnosed with NGU as men who did not have SPR. (p<0.001, Binomial Distribution Probability).

SPR is not present in normal healthy men. It is observed in men with nongonococcal urethritis, in whom it occurs in great numbers. I have also discovered that SPR can cause disease in other organ systems, and in fact can cause systemic disease. Infection with SPR can cause colitis, pelvic inflammatory disease (PID), adentitis (swelling of the lymph nodes), and skin eruptions. All of these infections can be treated systemically as described below.

Accordingly, the invention features a biologically pure culture of the single-celled organism Spiky Rotating Cells (SPR). Preferably, the culture has the biological characteristics of the SPR sample, ATCC Deposit No. PTA-2129, received at the ATCC on Jun. 18, 2000. The SPR organisms of the culture preferably exhibits the following biological characteristics (a) spherical shape, (b) motile in an imperfect rotating manner, (c) multiple spiky membrane projections, (d) highly refractile cell membrane when viewed, e.g., by Darkfield microscopy. Preferably, further characteristics are: (e) approximately 7–8 $\mu$m in diameter, (f) provisionally classified as a protozoan, (g) periodic colonial morphology, and (h) preferential proliferation in Diamond's Media.

The identification of the new SPR organism permits the diagnosis of an SPR infection in a human patient by the steps of: (a) obtaining a sample, e.g., a pus sample from the reproductive or other organ system, and (b) testing the sample for the presence of SPR. Where the patient is a male, the collection step preferably involves collecting a secretion from the urethra of the patient. This can be carried out using a novel collection device that includes a handle portion which is attached to means for collecting secretions from the reproductive system of the male patient, and which also includes a pH sensor positioned adjacent to the collecting means so that it can come into contact with the sample and provide an indication of the pH of the sample, which is useful in aiding in the diagnosis of a SPR infection. Preferably, the collecting means of the instrument is adapted so that it can be inserted into the distal end of the urethra of the male patient. It may also be used for diagnosis in females, by sampling cervico vaginal secretions; and in skin or other organ infections by sampling pus.

My discovery of the novel SPR organism also provides for the treatment of SPR infections in male and female patients. The method involves first diagnosing the SPR infection, and then, upon obtaining a positive diagnosis, administering to the patient an SPR-inhibiting amount of an anti-SPR agent selected from the group consisting of itraconazole, ofloxacin, metronidazole.

By "biologically pure culture" is meant a culture of SPR in which the predominant pathogen, numerically, is SPR, present in the culture in greater proportion than occurs in naturally occurring human urethral or other secretions.

DETAILED DESCRIPTION

Sampling

SPR occurs in a naturally contaminated environment, the human genital tract, skin and other organs. Biologically pure cultures of SPR are obtained in a process that begins with sampling, carried out as follows.

Figure 1:
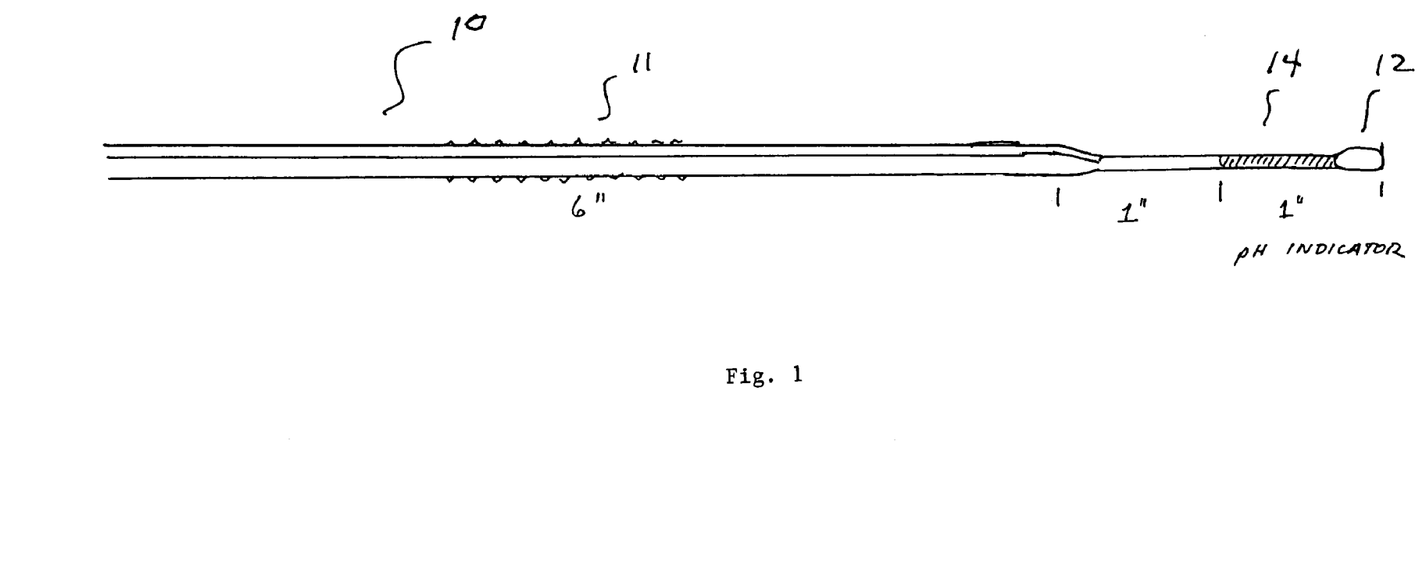
FIG. 1 is a plan view of a secretion sampling instrument of the invention.
Figure 2:
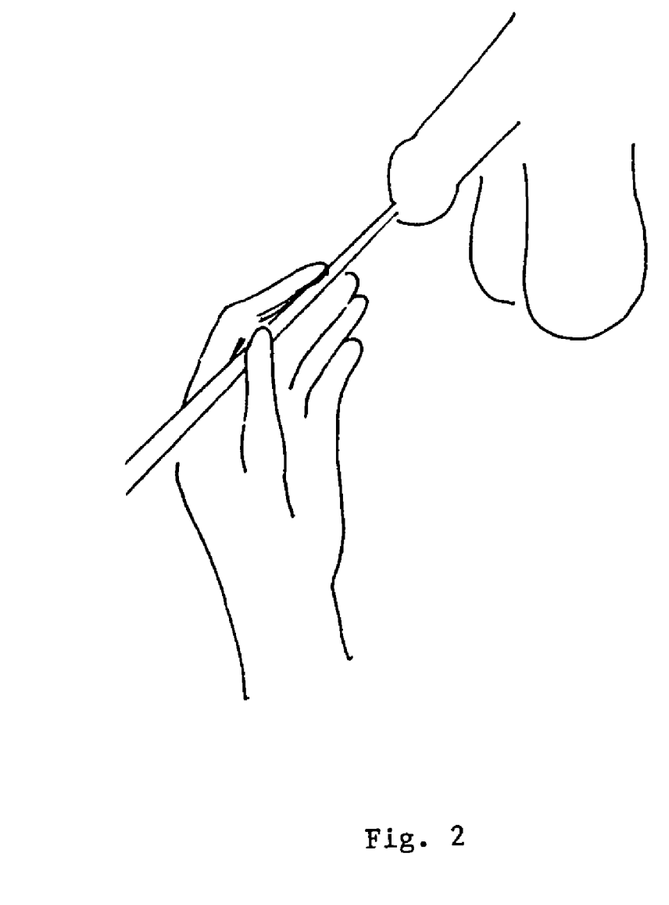
FIG. 2 is a plan view of the sampling instrument in operation.
Figure 3:
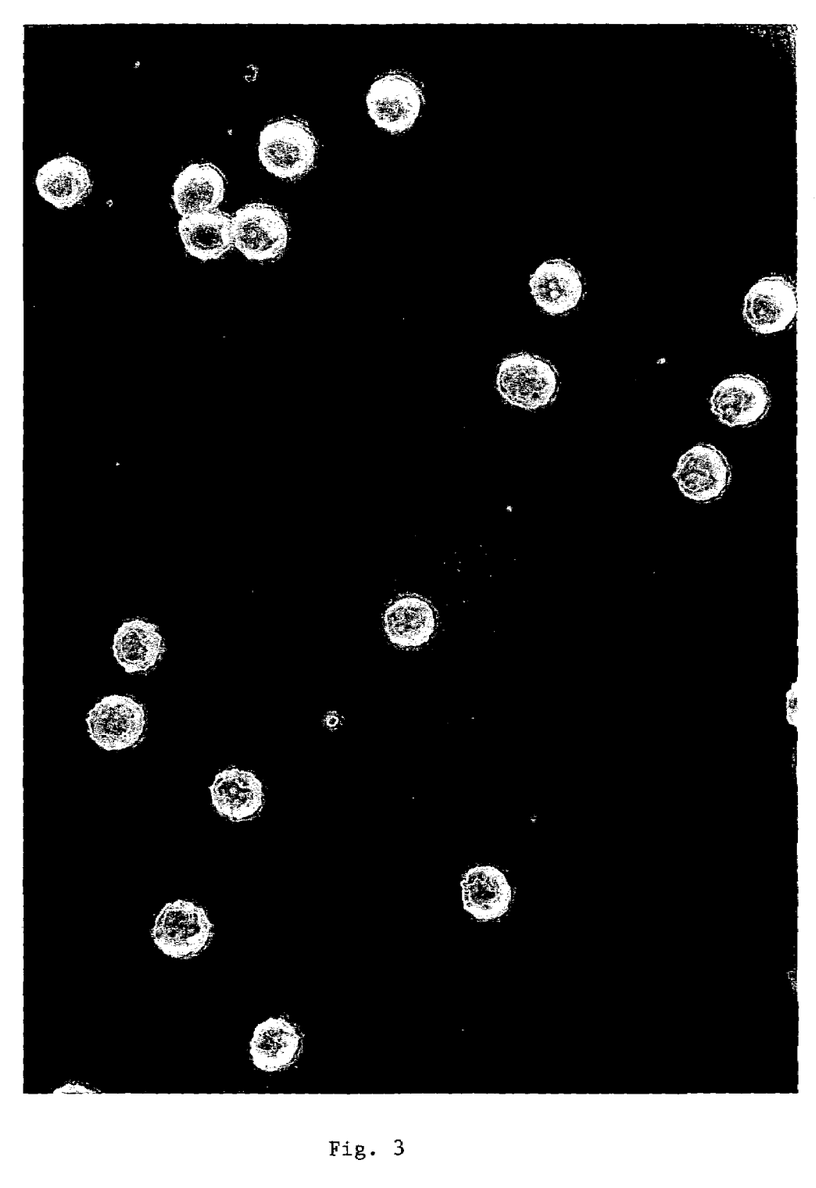
FIG. 3 is a Dark field micrograph of individual SPR organisms.
Figure 4:
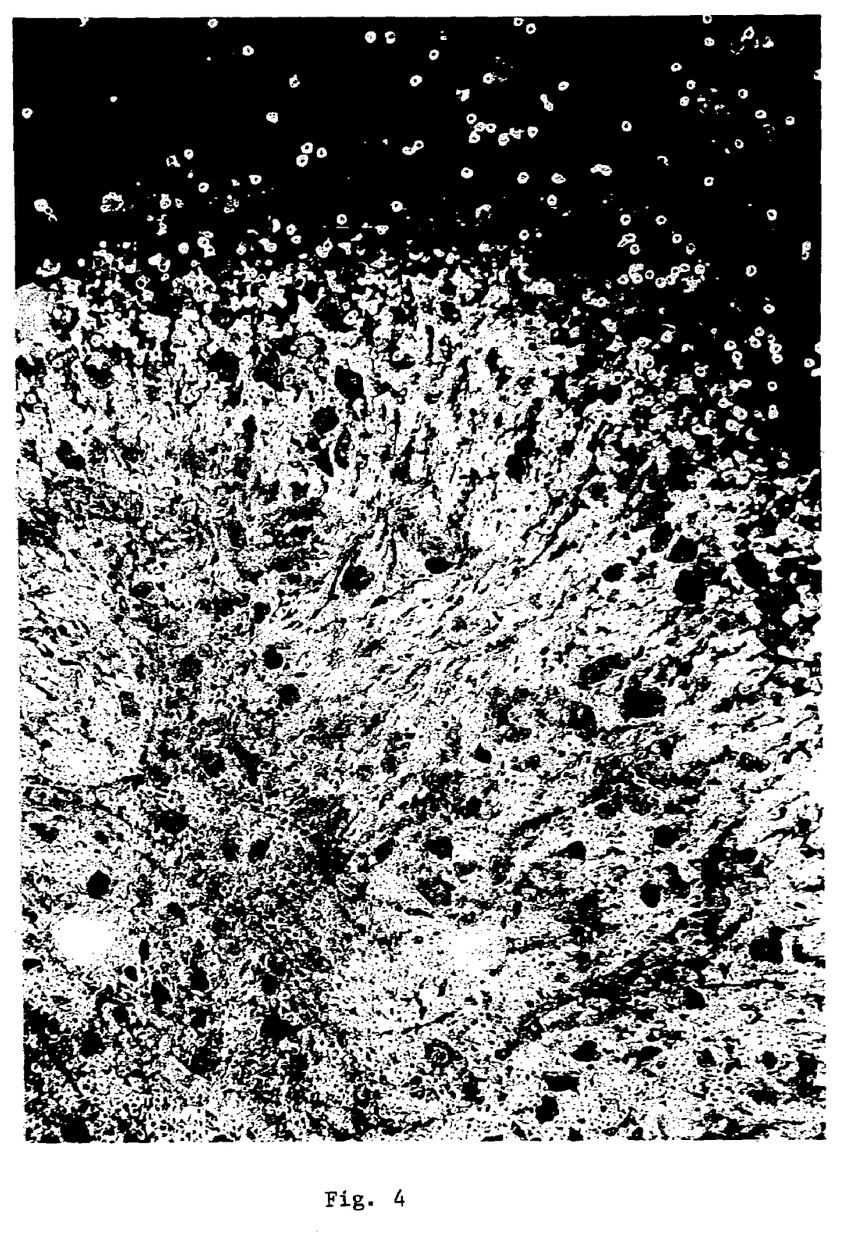
FIG. 4 is a Dark field micrograph of colonial SPR organisms.

First, the region to be sampled, e.g., the urethra, the surface of the skin, or the cervix, is sterilized, e.g., with isopropyl alcohol, and allowed to air dry. Next, a sample is collected from the region of interest. Referring to FIG. 1, if the sample is to be obtained from the male urethra a sampling instrument is employed. The instrument consists of a handle portion 10 with gripping region 11; the handle extends to the collecting means 12, which in this embodiment is a streaking loop commonly used to plate microorganisms. Adjacent to loop 12 is a region 14 that has been rendered a pH sensor, e.g., by wrapping the region with pH indicator tape. Referring to FIG. 2, the sampling instrument of FIG. 1 is inserted approximately 1–2 cm into the distal end of the male urethra and then withdrawn, bringing with it a secretion sample from the urethra, in such a way that some of the sample contacts the pH sensor 14 of the instrument.

After the sample has contacted the pH sensor, the pH of the secretion is determined as a step in the diagnosis of SPR. SPR infection, particularly where it is heavy infection, raises the pH of the secretions, which normally is in the range of 4.5–5. A pH greater than about 6.0 is indicative of an SPR infection, and a heavy infection can cause the pH reading to be as high as 7.5.

These foregoing steps are repeated a sufficient number of times to result in the collection of 0.5–1 microliter of secretion.

Identification

In the next step, identification of SPR, the collected secretion is diluted in 1–2 drops of normal saline. The diluted sample is then covered with a cover slip and examined immediately by microscopy. The organism is identified by observing the morphologic characteristics of SPR summarized above, and is best carried out by using a Darkfield microscope. Preferably, there are sufficient organisms so that they can be observed at various stages in the life cycle of the organism. As is discussed above, in its solitary living stage, each SPR is a motile, spherical organism, most probably a protozoan, with a diameter of 7 $\mu$m–8 $\mu$m. It has a highly refractile membrane with characteristic spikes, and moves in a peculiar rotary manner across the microscope field. The organism may also be observed under conventional light microscopy and appears as a pale yellowish green sphere.

The organisms also exhibit a characteristic colonial clustering morphology in which many organisms come together to form large colonies.

Culture

The SPR organism can be selectively cultured in modified Diamond's Medium (LS Diamond, *J. Parasit*, (43):488–90 (1957)).

In order to prevent overgrowth of contaminating microorganisms, the Diamond's Medium is modified as follows. To 100 ml of medium are added 500 mg cycloheximide and 40 mg of chloramphenicol. The pH of the medium is adjusted to 6.8–7-0, and sterilized by autoclaving for ten minutes at 15 pounds of pressure.

The SPR organisms are inoculated, using the collecting instrument of FIG. 1, into the modified Diamond's Medium; 2–3 $\mu$l sample are inoculated into 3 ml medium. The inoculated medium is stoppered loosely and incubated at 36° C. in a 5% $CO_2$ enhanced atmosphere for 3–4 days. These conditions selectively bring about the proliferation of the SPR organism compared to other contaminating organisms.

The presence of SPR organisms is confirmed by gently decanting the top two-2.5 ml of fluid from the culture tube, and then aspirating the sediment from the tube using a sterile needle and syringe. A drop of sediment is then placed on a slide under a cover slip and examined for the characteristic morphologic traits of the SPR organism, as described above.

Purification

The SPR organism is cultured in the medium described above for 96–120 hours, after which time the top 2–2.5 ml of fluid is gently decanted from the culture tube. Using a sterile needle and syringe, the sediment is aspirated and examined for SPR. The SPR is then inoculated into a fresh tube of selective, modified Diamond's Medium, and these steps are repeated as often as necessary to obtain a biologically pure culture. The purity of the culture is confirmed by inoculating the culture into a brain-heart infusion and thioglycollate broth, and then testing for the absence of contaminating microorganisms.

Treatment

I have found that several commercially available drugs are effective in treating infection with SPR. One such drug is itraconazole, sold under the trade name SPORANOX®, available from Jansen Pharmaceuticals. The patient ingests one 200 mg tablet per day for three-four weeks.

Another drug that can be used to treat SPR infection is metronidazole, sold under the trade name FLAGYL®. The patient takes 500 mg twice per day for six weeks.

Yet another drug that is effective in treating SPR infection is ofloxacin, sold under the trade name FLOXIN®. The patient takes 400 mg twice per day for two weeks.

Deposit

A biologically pure culture, as defined herein, of SPR was deposited with the American Type Culture Collection, 10801 University Boulevard, Manassas, Va. 20110–2209 on Jun. 18, 2000, and given ATCC accession number PTA-2129.

This deposit was made under the provisions of the Budapest Treaty on the International Recognition of the Deposit of Microorganisms for the Purpose of Patent Procedure and the Regulations thereunder ("Budapest Treaty"). This assures maintenance of viable cultures for 30 years from the date of the deposit. The organisms will be made available by ATCC under the terms of the Budapest Treaty, and subject to an agreement between myself and ATCC, which assures permanent and unrestricted availability of the cultures to the public upon issuance of the pertinent U.S. patent or upon laying open to the public of any U.S. or foreign patent application, whichever comes first, and assures availability of the cultures to one determined by the U.S. Commissioner of Patent and Trademarks to be entitled thereto according to 35 U.S.C. §122 and the Commissioner's rules pursuant thereto (including 37 C.F.R. §1.12 with particular reference to 886 OG 638).

In respect of those designations in which a European patent is sought, a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample.

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

Other Embodiments

Other embodiments are within the following claims. For example, in diagnostic tests for SPR, rather than identifying the organism microscopically, it can be identified using other known methods. One such class of methods, immunological identification, employs antibodies specific for SPR, in any of the many conventional immunoassay formats, e.g., ELISA tests using, e.g., enzymes such as horseradish peroxidase. The SPR-specific antibody used in such an assay can be polyclonal or monoclonal, and can be produced using conventional methods, e.g., challenging a rabbit or mouse with the SPR organism and then obtaining the antibody using conventional techniques.

Other diagnostic tests for SPR can be nucleic acid based. One class of such tests employs DNA probes that specifically hybridize to unique regions of the genome or ribosomal RNA of the SPR organism. Alternatively, the diagnostic assay can employ RNA/DNA amplification, e.g., PCR/TMA or Q-beta replicase amplification, using primers unique to the SPR genome.

What is claimed is:

1. A biologically pure culture of a single-celled organism, Spiky Rotating Cells (SPR), having all of the characteristics of the deposited single-celled organism having the accession number ATCC PTA-2129, wherein said organism causes disease in humans and comprises the following biological characteristics: (i) provisional classification as a protozoan, (ii) a spherical shape measuring approximately 7–8 $\mu$m as a solitary single-celled organism, (iii) a refractile cell membrane, (iv) multiple circumferential spiky projections of the cell membrane, (v) rotatory motility, (vi) periodic clustering behavior to form colonies, and (vii) existence in an extracellular environment.

2. The culture of claim 1, wherein said extracellular environment is skin, fluid of the genital tract, or the extracellular fluid of other organs.

3. The culture of claim 1, wherein said disease is nongonococcal urethritis.

4. The culture of claim 1, wherein said organism proliferates in Diamond's media.

5. A method of diagnosing an SPR infection in a human patient, said method comprising the steps of:
   a) obtaining a sample from said patient; and
   b) testing said sample for the presence of an organism, having all of the characteristics of the deposited single-celled organism having the accession number ATCC PTA-2129, that causes disease in humans, said organism having the following biological characteristics: (i) provisional classification as a protozoan, (ii) a spherical shape measuring approximately 7–8 $\mu$m as a solitary single-celled organism, (iii) a refractile cell membrane, (iv) multiple circumferential spiky projections of the cell membrane, (v) rotatory motility, (vi) periodic clustering behavior to form colonies, and (vii) existence in an extracellular environment.

6. The method of claim 5, wherein said method further comprises, after step a), testing the pH of said sample, wherein a pH greater than 6.0 is further indicative of the presence of said SPR infection.

7. The method of claim 5, wherein said patient is a male, and wherein step a) comprises obtaining said sample from the urethra of said male patient, wherein said sample comprises a secretion found in the urethra of said male patient.

8. The method of claim 5, wherein step b) comprises admixing said sample with saline and examining said sample by microscopy, wherein said SPR infection is confirmed by the presence of an organism comprising said biological characteristics.

9. The method of claim 8, wherein said extracellular environment is skin, fluid of the genital tract, or the extracellular fluid of an organ.

10. The method of claim 8, wherein said organism proliferates in Diamond's media.

11. The method of claim 5, wherein said patient is a female, and wherein step a) comprises obtaining a sample from the vagina of said female patient, wherein said sample comprises a cervico vaginal secretion from said female patient.

12. The method of claim 5, wherein said patient has a skin eruption or lymph node abscess, and wherein the sample of step a) comprises a secretion from said skin eruption or abscess.

13. An instrument for collecting a sample from a male patient, wherein said sample comprises urethral secretions, said instrument comprising:
   a) a handle portion;
   b) attached to said handle portion, a means for collecting a secretion from the reproductive system of said male patient, wherein said collecting means is sized and shaped for insertion into the distal end of the urethra of said male patient and comprises a loop region with an opening, wherein said loop region is positioned at the end of said device opposite said handle portion; and
   c) a pH sensor positioned adjacent the collecting means, wherein said pH sensor comes into contact with said sample and detects the pH of said sample.

14. An instrument for collecting a sample from a female patient, wherein said sample comprises cervico vaginal secretions, and detecting the presence of SPR in said secretions, said instrument comprising:
   a) a handle portion;
   b) attached to said handle portion, a means for collecting cervico vaginal secretions from said female patient, wherein said collecting means comprises a loop region with an opening, wherein said loon region is positioned at the end of said device opposite said handle portion; and
   c) a pH sensor positioned adjacent the collecting means, wherein said pH sensor comes into contact with said sample and detects the pH of said sample.

15. A method of treating an SPR infection in a patient, said method comprising the steps of:
   a) diagnosing said SPR infection, wherein the organism causing said SPR infection causes disease in human and comprises all of the characteristics of the deposited single-celled organism having the accession number ATCC PTA-2129 and the following biological characteristics: (i) provisional classification as a protozoan, (ii) a spherical shape measuring approximately 7–8 $\mu$m as a solitary single-celled organism, (iii) a retractile cell membrane, (iv) multiple circumferential spiky projections of the cell membrane, (v) rotatory motility, (vi) periodic clustering behavior to form colonies, and (vii) existence in an extracellular environment; and b) upon obtaining a positive diagnosis in step a), administering to said patient an SPR inhibiting amount of an anti-SPR agent selected from the group consisting of itraconazole, ofloxacin and metronidazole.

16. A single-celled organism having accession number ATCC PTA-2129.

* * * * *